US010232575B2

(12) United States Patent
Perkins et al.

(10) Patent No.: US 10,232,575 B2
(45) Date of Patent: Mar. 19, 2019

(54) METHOD FOR FABRICATION CONTROL OF AN OPTICAL INTEGRATED COMPUTATIONAL ELEMENT

(71) Applicant: Halliburton Energy Services, Inc., Houston, TX (US)

(72) Inventors: David L. Perkins, The Woodlands, TX (US); Michael N. Simcock, Columbia, SC (US)

(73) Assignee: Halliburton Energy Services, Inc., Houston, TX (US)

( * ) Notice: Subject to any disclaimer, the term of this patent is extended or adjusted under 35 U.S.C. 154(b) by 340 days.

(21) Appl. No.: 15/035,179

(22) PCT Filed: Dec. 4, 2013

(86) PCT No.: PCT/US2013/073182
§ 371 (c)(1),
(2) Date: May 6, 2016

(87) PCT Pub. No.: WO2015/084351
PCT Pub. Date: Jun. 11, 2015

(65) Prior Publication Data
US 2016/0288436 A1    Oct. 6, 2016

(51) Int. Cl.
*B29D 11/00* (2006.01)
*G02B 5/28* (2006.01)
*G01N 21/25* (2006.01)

(52) U.S. Cl.
CPC .. *B29D 11/00634* (2013.01); *B29D 11/00961* (2013.01); *G01N 21/25* (2013.01); *G02B 5/285* (2013.01)

(58) Field of Classification Search
CPC ........ B29D 11/00634; B29D 11/00961; G02B 5/285; G01N 21/25
See application file for complete search history.

(56) References Cited

U.S. PATENT DOCUMENTS

| | | | |
|---|---|---|---|
| 6,940,595 B1 | 9/2005 | Johs et al. | |
| 7,901,870 B1 * | 3/2011 | Wach | G02B 5/285 430/321 |
| 2003/0072869 A1 | 4/2003 | Decusatis et al. | |
| 2003/0103218 A1 | 6/2003 | Niu et al. | |
| 2010/0165134 A1 | 7/2010 | Dowski, Jr. et al. | |
| 2013/0287061 A1 | 10/2013 | Freese et al. | |

OTHER PUBLICATIONS

International Search Report and Written Opinion dated Apr. 18, 2014; International PCT Application No. PCT/US2013/073182.

* cited by examiner

*Primary Examiner* — Mathieu D Vargot
(74) *Attorney, Agent, or Firm* — McGuire Woods LLP

(57) ABSTRACT

A method controls fabrication of a multi-layered integrated computational element designed to have a target optical spectrum. A transfer function is generated relating a blue wavelength, shift between an as-annealed optical spectrum and an as-fabricated optical spectrum of a first integrated computational element at a standard temperature. Using the transfer function, an initial compensating red shift is incorporated into a second integrated computational element such that the as-annealed optical spectrum of the second integrated computational element matches the target optical spectrum.

13 Claims, 10 Drawing Sheets

METHOD FOR FABRICATION CONTROL OF AN OPTICAL INTEGRATED COMPUTATIONAL ELEMENT

The present invention generally relates to methods of optical chemical analysis and, more specifically, to the fabrication and characterization of optical integrated computational elements (ICE).

An ICE may comprise a multilayered optical interference filter that is designed to transmit a predetermined target spectrum. The target optical spectrum may be indicative of a characteristic of interest of a material sample. The various embodiments of the disclosed optical computing device may be suitable for use in the oil and gas industry.

Fabrication of such optical elements may be done in a batch process. The elements may exhibit some variability in their optical spectrum both between elements and relative to a desired target spectrum. In addition, heating of such elements to elevated operating temperatures may result in variable hysteresis.

The present application provides methods to characterize at least these variabilities and to provide techniques to correct and/or account for such variabilities.

BRIEF DESCRIPTION OF THE DRAWINGS

A better understanding of the present invention can be obtained when the following detailed description of example embodiments are considered in conjunction with the following drawings, in which.

DETAILED DESCRIPTION

Figure 1:
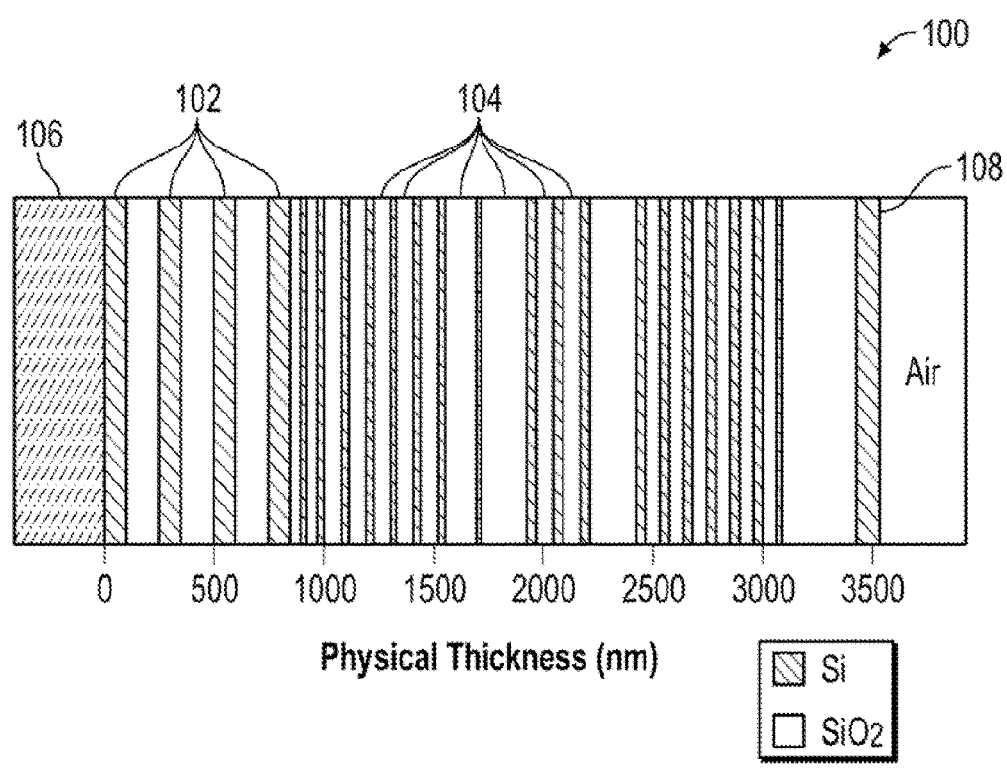
FIG. 1 shows an exemplary multilayered ICE.

ICE may be used in qualitative or quantitative analysis of materials and contain a carefully-crafted optical spectrum that is based on the chemometric analysis of data from which they are designed. These elements can be crafted by modeling of the element in order to select the material thicknesses and the material refractive indices used in the element. Such an ICE is capable of distinguishing electromagnetic radiation related to a particular characteristic, or analyte, of interest of a sample substance from other electromagnetic radiation related to other characteristics or analytes of other components of a sample substance.

Such optical elements may be produced in a batch process. However optical elements produced in a batch may have some variability, which may be especially pronounced with ICE since the layer structure is generally arbitrary to any metric other than the spectroscopic data to which they were designed.

Such an ICE may be designed to exhibit a target optical spectrum for detecting a predetermined fluid characteristic or analyte. In addition, in some uses, for example, downhole hydrocarbon well applications, the ICE may be subjected to temperatures significantly above the traditional design temperatures, and the ICE may exhibit unrecoverable spectral drift in its transmission spectrum. The present disclosure provides methods for identifying such spectral drift and to provide annealing methods to shift the operational transmission spectrum to an acceptable range with respect to the target spectrum.

As used herein, the term "fluid" refers to any substance that is capable of flowing, including particulate solids, liquids, gases, slurries, emulsions, powders, muds, glasses, combinations thereof, and the like. In some embodiments, the fluid can be an aqueous fluid, including water or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid or a formation fluid. Fluids can include various flowable mixtures of solids, liquids and/or gases. Illustrative gases that can be considered fluids according to the present embodiments include, for example, air, nitrogen, carbon dioxide, argon, helium, hydrogen disulfide, mercaptan, thiophene, methane, ethane, butane, and other hydrocarbon gases, combinations thereof and/or the like.

As used herein, the term "characteristic" refers to a chemical, mechanical, or physical property of a substance. A characteristic of a substance may include a quantitative value of one or more chemical components therein. Such chemical components may be referred to herein as "analytes." Illustrative characteristics of a substance that can be monitored with the ICE disclosed herein can include, for example, chemical composition e.g., identity and concentration, in total or of individual components, impurity content, pH, viscosity, density, ionic strength, total dissolved solids, salt content, porosity, opacity, bacteria content, combinations thereof, and the like.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation from a substance or sample of the substance and produce an output of electromagnetic radiation from a processing element. The processing element may be, for example, an integrated computational element. The electromagnetic radiation emanating from the processing element is changed in some way so as to be readable by a detector, such that an output of the detector can be correlated to at least one characteristic of the substance. The output of electromagnetic radiation from the processing element can be reflected electromagnetic radiation, transmitted electromagnetic radiation, and/or dispersed electromagnetic radiation. As will be appreciated by those skilled in the art, whether reflected, transmitted, and/or dispersed electromagnetic radiation is analyzed by the detector will be a matter of routine experimental design. In addition, emission and/or scattering of the substance, for example via fluorescence, luminescence, radiation and re-radiation, Raman scattering, and/or Raleigh scattering can also be monitored by the optical computing devices.

As used herein, the term "optically interact", or variations thereof, refers to the reflection, transmission, scattering, diffraction, or absorption of electromagnetic radiation either on, through, or from one or more processing elements, such as integrated computational elements. Accordingly, optically interacted light refers to light that has been reflected, transmitted, scattered, diffracted, or absorbed by, emitted, or re-radiated, for example, using the ICE, but may also apply to interaction with a sample substance or other system optical components.

As used herein, the term "sample," or variations thereof, refers to at least a portion of a substance of interest to be tested or otherwise evaluated using the optical computing devices described herein. The sample includes the characteristic of interest, as defined above, and may be any fluid, as defined herein, or otherwise any solid substance or material such as, but not limited to, rock formations, concrete, other solid surfaces, etc.

When electromagnetic radiation interacts with a substance, unique physical and chemical information about the substance may be encoded in the electromagnetic radiation that is reflected from, transmitted through, or dispersed from the sample. This information is often referred to as the substance's spectral "fingerprint." At least in some embodiments, the exemplary ICE disclosed herein are capable of extracting the information of the spectral fingerprint of at least one characteristic or analyte within a substance and converting that information into a detectable output regarding the overall properties of a sample. That is, through suitable configurations of the exemplary ICE, electromagnetic radiation associated with characteristics or analytes of interest in a substance can be separated from electromagnetic radiation associated with all other components of a sample in order to estimate the sample's properties in real-time or near real-time.

Referring to FIG. 1, illustrated is an exemplary ICE 100. As illustrated, ICE 100 may include a plurality of material layers 102 and 104. In general, these layers consist of materials whose index of refraction varies from layer to layer. In one example, the layers may have an alternating high and low index of refraction, respectively. Examples of materials may comprise silicon (Si) and $SiO_2$ (quartz), niobia and niobium, germanium and germania, MgF, SiO, $Al_2O_3$, $TiO_2$, and other high and low index materials known in the art. In one example, low index of refraction materials may include those materials with a refractive index between about 1 to about 2. Similarly, high index of refraction materials may include those materials with a refractive index between about 3 to about 4. The layers 102, 104 may be strategically deposited on an optical substrate 106. In some embodiments, the optical substrate 106 is BK-7 optical glass. In other embodiments, the optical substrate 106 may be other types of optical substrates, such as quartz, sapphire, silicon, germanium, zinc selenide, zinc sulfide, or various plastics, for example, polycarbonate, polymethylmethacrylate (PMMA), polyvinylchloride (PVC), diamond, ceramics, combinations thereof, and the like. At the opposite end (e.g., opposite the optical substrate 106), the ICE 100 may include a layer 108 that is generally exposed to the environment of the device or installation. The number of layers 102, 104 and the thickness of each layer 102, 104 may be determined from the spectral attributes acquired from a spectroscopic analysis of a characteristic of the sample substance using a conventional spectroscopic instrument. The spectrum of interest of a given characteristic of a sample typically includes any number of different wavelengths. It should be understood that the exemplary ICE 100 in FIG. 1 does not, in fact, represent any particular characteristic of a given sample, but is provided for purposes of illustration only. Consequently, the number of layers 102, 104 and their relative thicknesses, as shown in FIG. 1, bear no correlation to any particular characteristic of a given sample. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the material to the sample substance.

The multiple layers 102, 104 may exhibit different refractive indices. By properly selecting the materials of the layers 102, 104, and their relative spacing, the exemplary ICE 100 may be configured to selectively pass/reflect/refract predetermined fractions of electromagnetic radiation at different wavelengths. Each wavelength is given a predetermined weighting or loading factor. The thicknesses and spacing of the layers 102, 104 may be determined using a variety of approximation methods from the spectrograph of the characteristic or analyte of interest. As a result, the output light intensity of the ICE 100 is related to the characteristic or analyte of interest. In one example, a computer program distributed under the name TFCALC by Software Spectra, Inc. of Portland, Oreg. may be used to execute this iterative method of designing the multiple thin film layers.

The above-described process can be used to design an ICE with a target optical spectrum for some nominal design temperature, for example 125 C. For simplicity, the discussion below is directed to an example using an optical transmission spectrum, with the understanding that the example is interchangeable with reflection and dispersion spectra. Such an ICE may be fabricated using known techniques and the as-fabricated optical spectrum may be measured and compared to the target spectrum using known methods. For example one comparison method calculates a merit function ("MF") that describes the difference between the target spectrum and the as-fabricated spectrum:

$$MF = \Sigma_W (T_c - T_t)^k / W,$$

where $T_c$ is the transmission percentage of the as-fabricated transmission spectrum at a given wavelength, $T_t$ is the transmission percentage of the target spectrum at the same wavelength, W is the number of wavelength channels measured and used in the merit function, and k is a constant. As should be understood in the art, constant k is a factor that determines the weighting applied in the MF to higher order differences between $T_c$ and $T_t$. If k is equal to 1, the merit function calculates average error between the two transmission spectra. A constant of 2 provides a mean square error. Acceptance of a particular design may be based an acceptable error between the two spectra. One, or more, iterations of this process may be required to acquire a suitable design resulting in the as-fabricated design having an acceptable spectrum at the standard test temperature.

Other merit functions may be used, for example:

$$MF = (1/W) \Sigma_W ((T_c - T_t)^k / T_{O1}) 1/k.$$

where $T_{O1}$ is the design tolerance.

Figure 2:
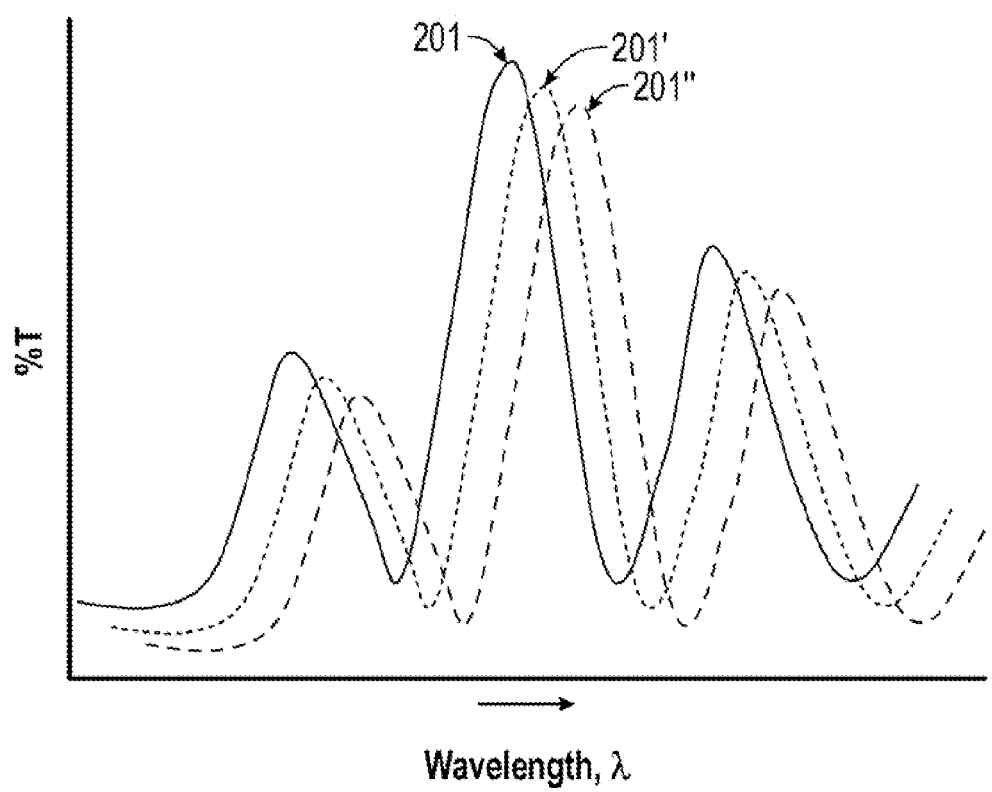
FIG. 2 shows the temperature cycle drift of an ICE

In order to have a useful ICE at high temperatures, additional processing may be required. It has been observed that when an ICE is cycled to high temperatures, the ICE transmission spectrum shifts toward the longer wavelengths, referred to herein as a "red shift". Upon cooling the ICE back to standard temperature the transmission spectrum shifts back toward the original spectrum, but, due to hysteresis, may be shifted from its original wavelengths. This is shown in FIG. 2 where a first temperature cycle results in the unpredictable shift of spectrum 201 of a theoretical ICE, at a standard temperature, from spectrum 201 to spectrum 201' and then spectrum 201" after successive temperature cycles to an elevated temperature. Such shifts may be due to continued chemical or crystallization of one or more of the layers of the ICE and may be unpredictable. This unpredictable drift would render the device unusable for downhole use where temperatures may cycle from the surface ambient temperature to downhole temperatures of 150 C to 200 C.

It has been determined that if the ICE is annealed at a temperature higher than the anticipated operating temperatures, the ICE structure may be stabilized, such that additional spectral drift is substantially eliminated for further operating temperature cycles. As used herein, annealing means heating an ICE up, from an ambient temperature, to a hither predetermined temperature, holding the ICE at that temperature for a predetermined time, and allowing the ICE to cool back down to the ambient temperature. The ICE may be exposed to air, or a protective gas during the annealing process.

Figure 3:
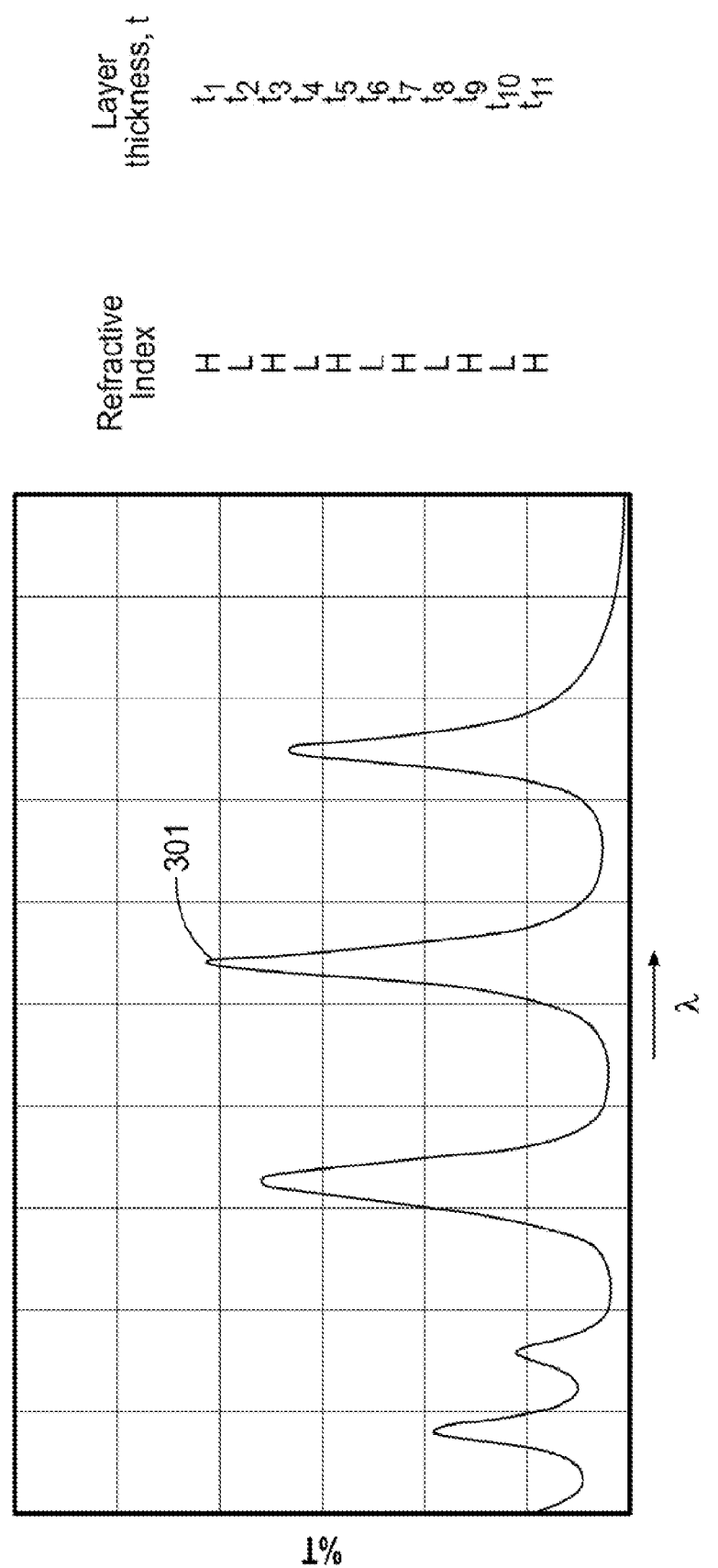
FIG. 3 shows the target spectrum and design thicknesses of an exemplary first ICE.
Figure 4:
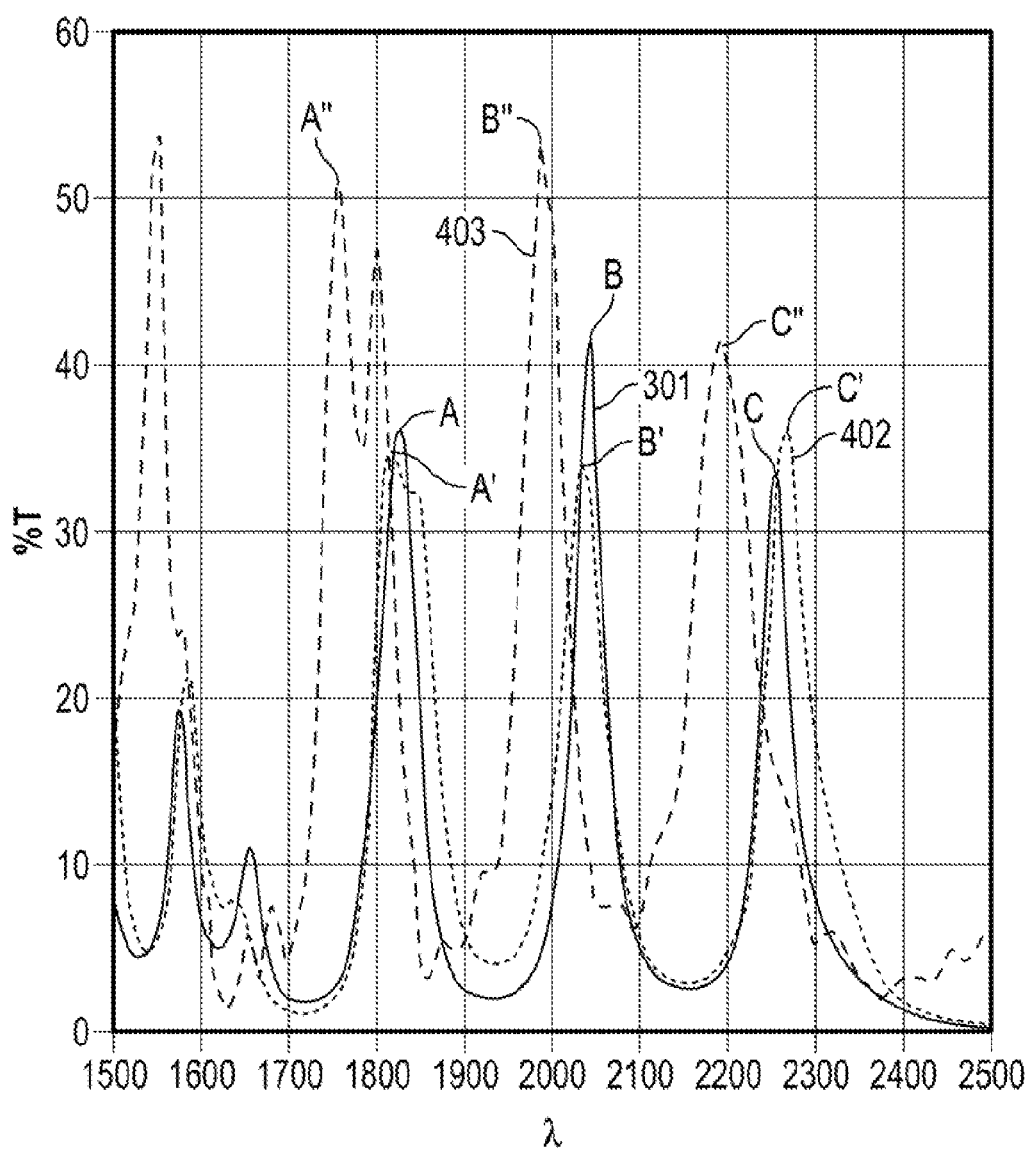
FIG. 4 shows the as-fabricated spectrum and blue shifted, as-annealed spectrum of the exemplary ICE described in FIG. 3.

Annealing, however, tends to produce a permanent shift in the spectrum toward the shorter wavelengths, referred to herein as a "blue shift." This effect is shown in FIGS. 3 and 4. FIG. 3 shows the relative design parameters for an ICE having a target transmission spectrum 301. The design has 11 layers of alternating thicknesses of high and low index of refraction materials. As indicated, each layer may have a different thickness, $t_i$. The target ICE transmission spectrum 301 corresponds to a characteristic of interest of the fluid sample.

Referring to FIG. 4, the 11 layer ICE design may be fabricated, using techniques known in the art, resulting in an as-fabricated spectrum 402 that is acceptably close to the target spectrum 301. As discussed above, if temperature cycled in this condition, unpredictable spectral shifting could occur with each cycle and render the ICE unusable for accurate quantitative measurement purposes. To obviate this problem, the ICE may be annealed. In one example, the fabricated ICE may be annealed at 300 C for a predetermined time of 12 hours, resulting in the substantially locked-in spectrum 403. Annealed spectrum 403 is blue-shifted to the shorter wavelengths, with greater transmission over the corresponding transmission values of both the target spectrum 301 and the as-fabricated spectrum 402. Annealing at other temperatures and/or for different durations, may result in different permanent blue shifts.

Figure 5:
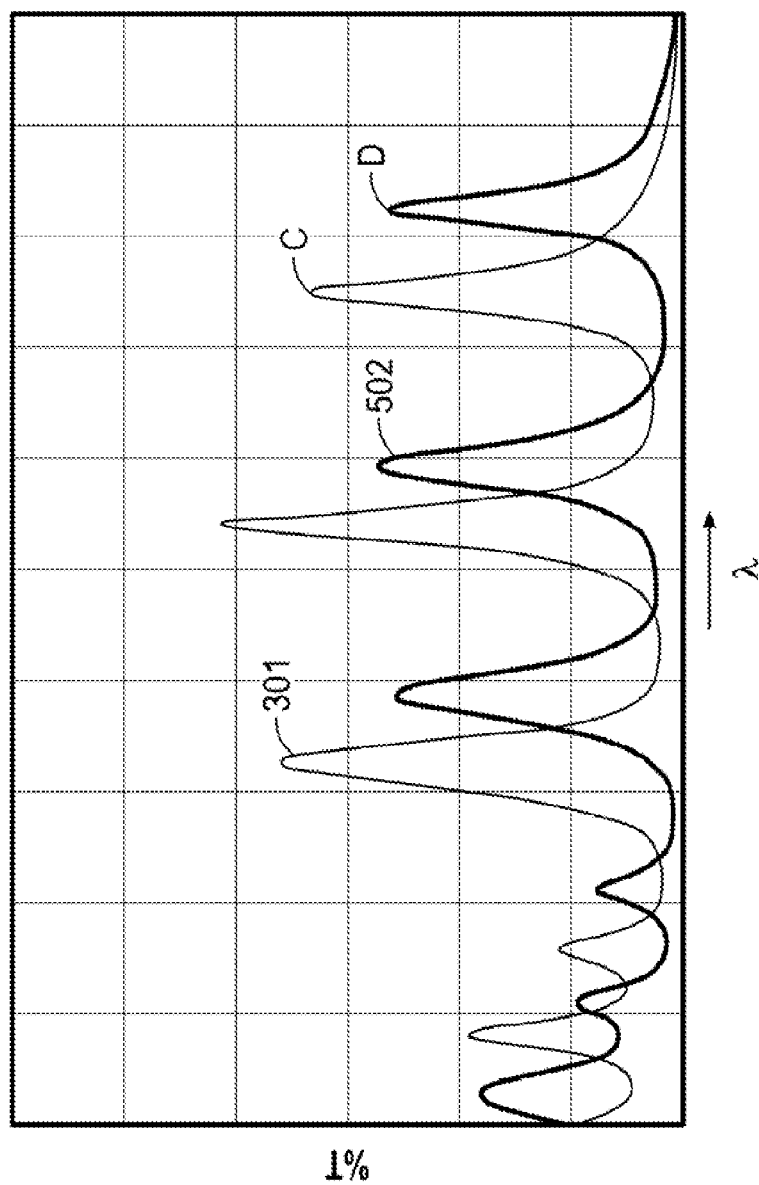
FIG. 5 shows the design thicknesses and the resulting spectrum for a pre-annealed red-shifted second ICE.
Figure 6:
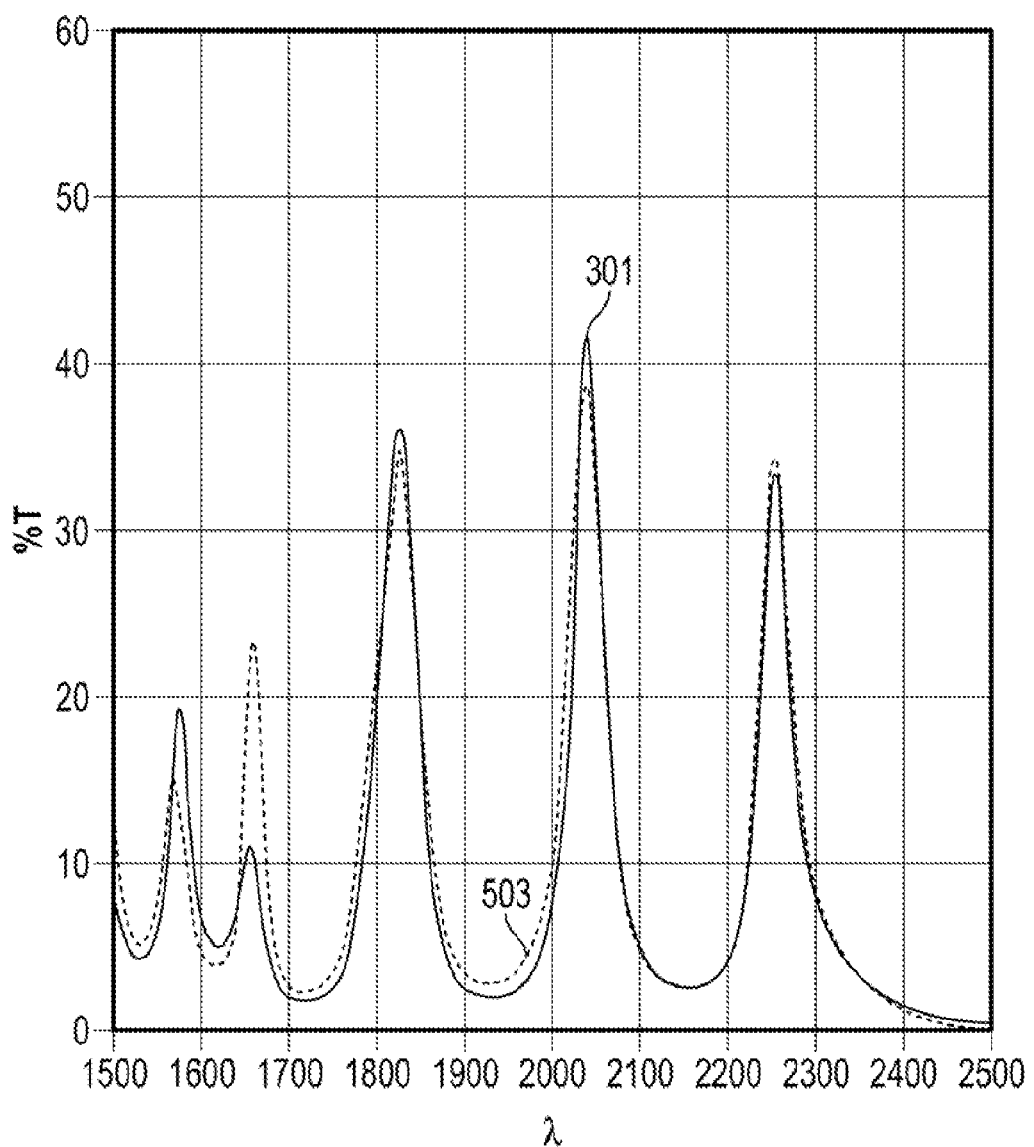
FIG. 6 shows the resulting as-annealed spectrum of the second ICE compared to the original target spectrum.

The original target spectrum 301 is selected because electromagnetic radiation emitted/transmitted/reflected by a sample in the target spectrum is correlatable to a characteristic of interest of a particular fluid sample. The annealed blue shifted spectrum 403 of FIG. 4 renders the annealed ICE unsuitable for transmitting the desired spectrum. In order to develop a suitable ICE having the desired target spectrum, a second ICE is designed that has an appropriate red shift, such that the annealing blue shift results in the desired target spectrum. To determine the appropriate red shift, a transfer function, TF, may be generated that may be used to generate an ICE design that has a pre-annealed red-shift and lower transmission with respect to the target design, such that subsequent annealing of the second ICE results in an as-annealed spectrum acceptably close to the target spectrum 301. This is shown in FIGS. 5 and 6. FIG. 5 shows a modified example layer thickness scheme to incorporate the red shift into the design, where $t+\delta t_i$ indicates an increased thickness, and $t-\delta t_i$ indicates a decreased thickness. While not shown, one skilled in the art will appreciate that modifications may also be incorporated in the index of refraction of each layer. As-fabricated spectrum 502 is the result of the red shifted design, and shows a shift to the longer wavelengths and a reduction in the amplitudes of the corresponding peaks, for example from peak C of spectrum 301 to peak D of spectrum 502. FIG. 6 shows the resulting post annealed (300 C for 12 hours) spectrum 503 of the second ICE, at the standard temperature, having substantially the same spectrum as target spectrum 301. The merit functions described previously may be used as a measure of the closeness of the post annealed and target spectrum. While described above with alternating layers of high and low index of refraction materials, one skilled in the art will realize that other combinations may be used. For example, consecutive low index layers, or high index layers of different materials may be present in the layer structure, as required to arrive at the target spectrum.

Figure 7:
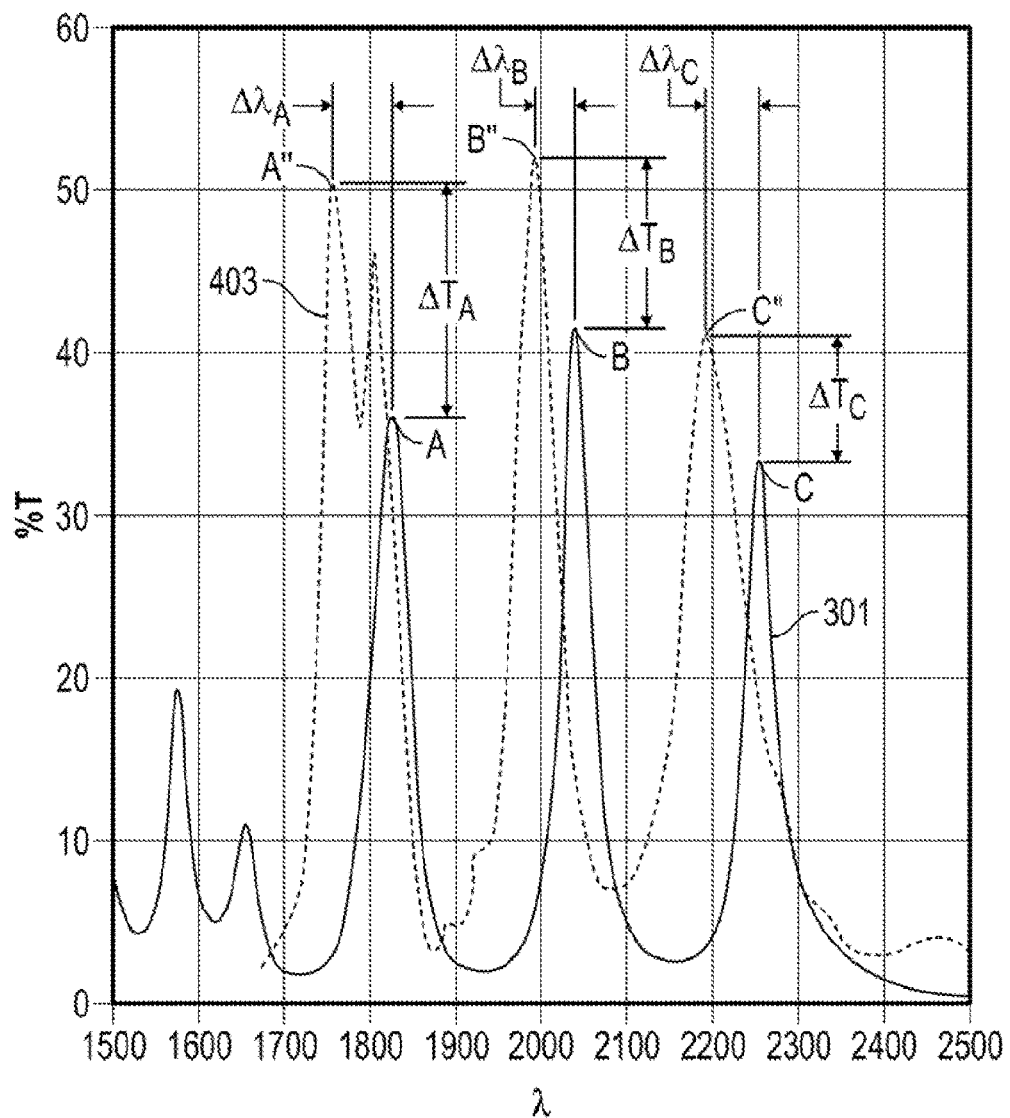
FIG. 7 shows an exemplary example for determining a transfer function for red shifting the second ICE design.

In one embodiment, the transfer function used to generate the second ICE may comprise a simple translation of peak frequency and transmission differences between the post annealed spectrum and the as-fabricated spectrum For example, see FIG. 7, where the differences in wavelength from the correlating peaks A-A", B-B", and C-C" are designated as $\Delta\lambda_A$, $\Delta\lambda_B$, and $\Delta\lambda_C$, respectively. In addition, the corresponding differences in transmission are designated as $\Delta T_A$, $\Delta T_B$, and $\Delta T_C$. In one example, the second ICE may be designed to have as-fabricated spectrum with corresponding peak frequencies red shifted by the absolute values of the amounts $\Delta\lambda_A$, $\Delta\lambda_B$, and $\Delta\lambda_C$. Similarly, the % transmission may be designed to be lower by the amounts $\Delta T_A$, $\Delta T_B$, and $\Delta T_C$, respectively. Alternatively, other transfer functions may be used. For example, the average blue shift of the as annealed peaks may be used as a red shift in a second ICE design. It is contemplated that any suitable transfer function be covered by the present disclosure. In one example, a batch of second ICE is fabricated. The same annealing process may be applied to all of the second ICE. Future batches of the same design second ICE may also use the same red shift design and the same annealing parameters. Note that the process outlined above, is repeated for each analyte and/or characteristic of interest of a fluid sample to be determined.

Figure 8:
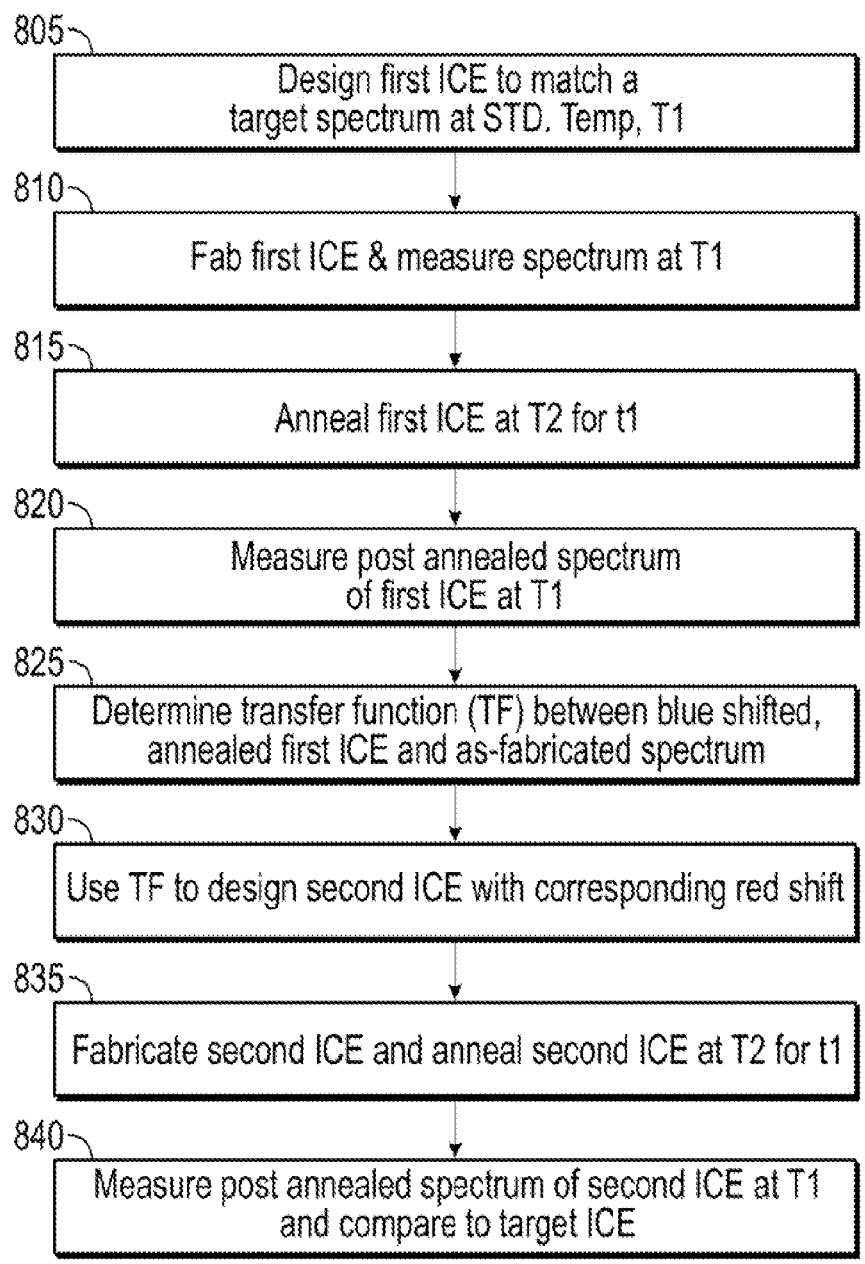
FIG. 8 shows a logic diagram for fabrication control of an ICE.

Using the techniques discussed above. FIG. 8 shows a method, also called a process, for fabrication control of an ICE to have a transmission spectrum that substantially matches a target spectrum, where:

in step 805, a first ICE is designed to have the target spectrum at a standard temperature, T1, for example 125 C;

in step 810, the first ICE is fabricated and the transmission spectrum of the first ICE is measured at T1;

in step 815, the first ICE is annealed at T2 for a time t1;

in step 820, the post annealed spectrum of the first ICE is measured at T1;

in step 825, a transfer function (TF) is determined between a blue shifted spectrum of the annealed first ICE and the as fabricated spectrum at T1;

in step 830, the TF is used to design a second ICE with a red shill to counteract the blue shift of annealing;

in step 835, the second ICE is fabricated and annealed at T2 for t1; and in step 840, the annealed spectrum of the second ICE is measured at T1 and compared to the target ICE spectrum to confirm an acceptable ICE.

Figure 9:
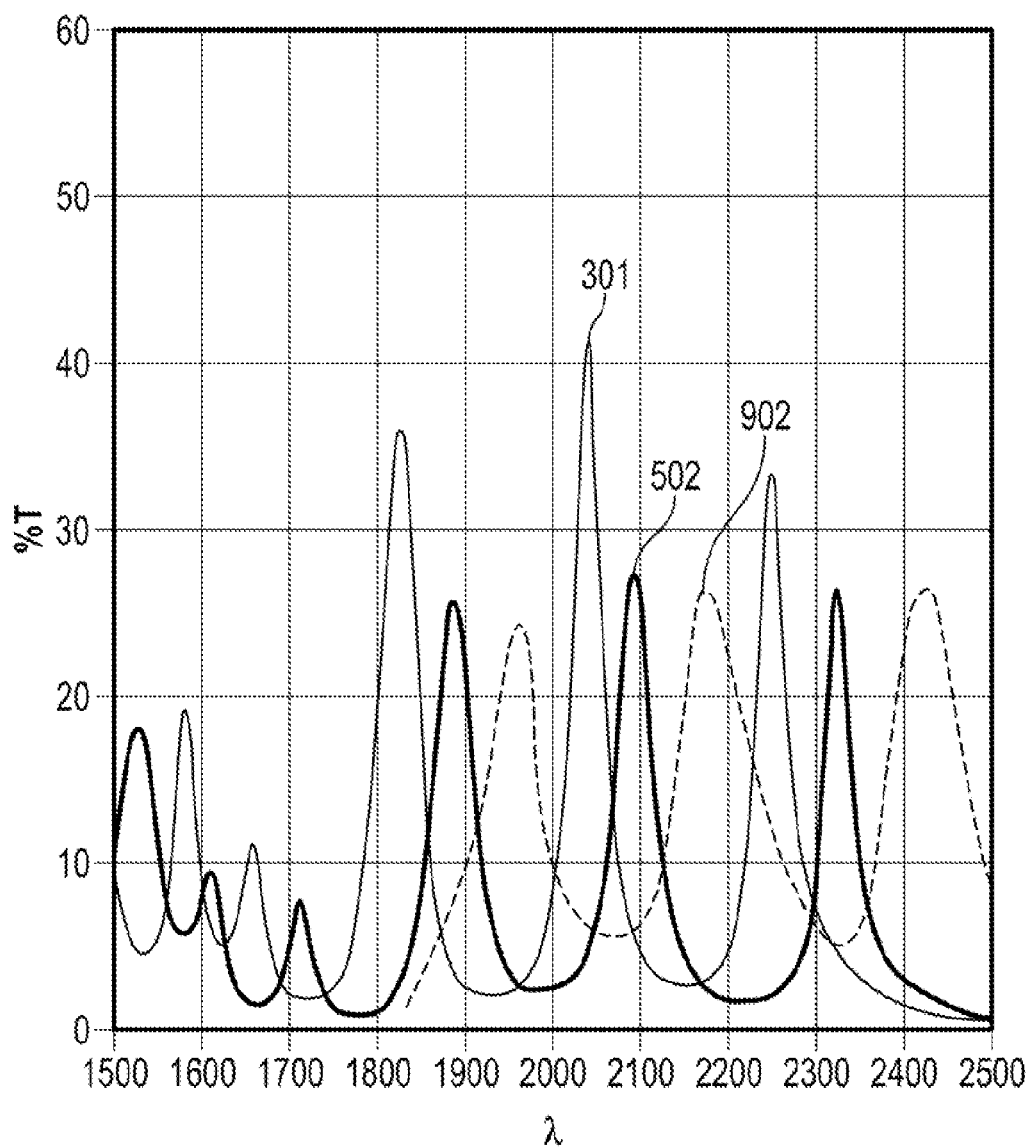
FIG. 9 shows a spectral variation in as-fabricated ICE from the same batch.
Figure 10:
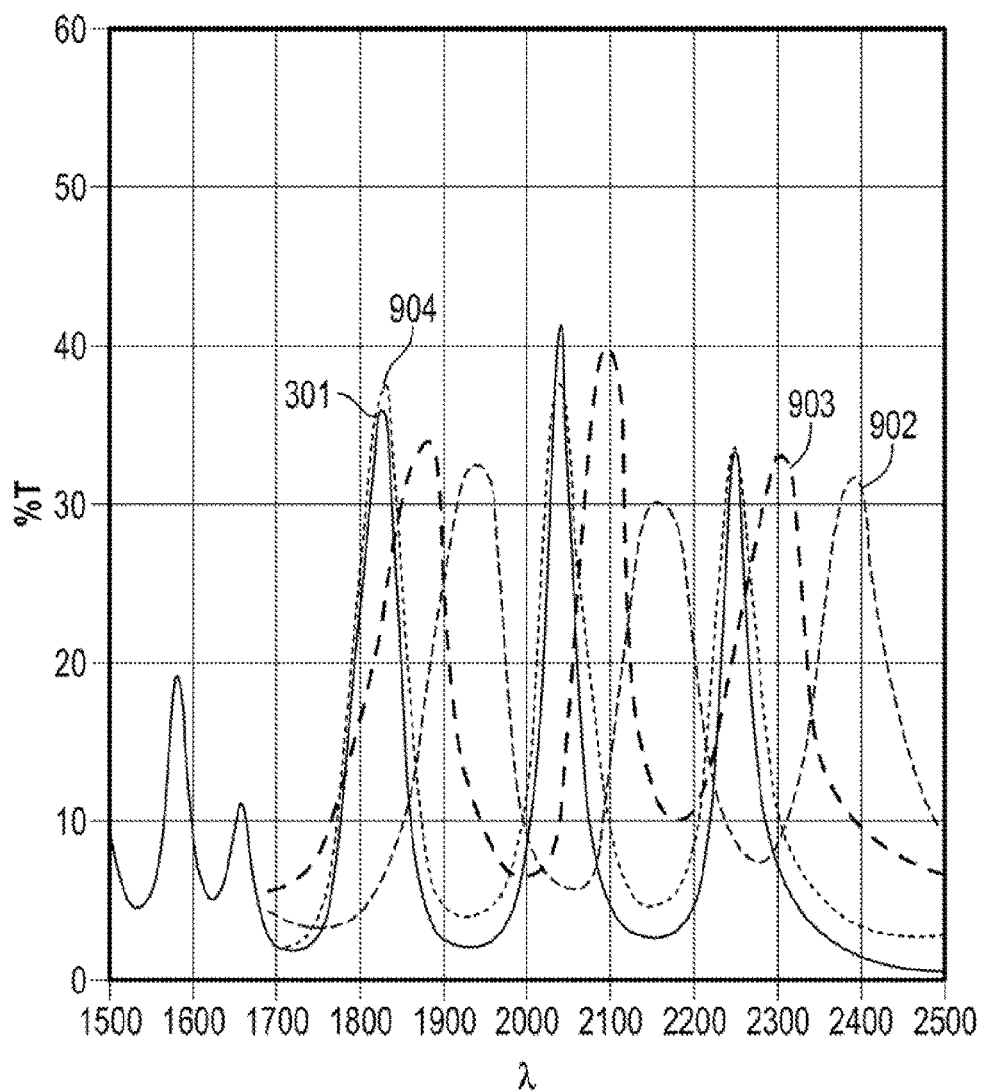
FIG. 10 shows a multi-step annealing process to correct the variation in the spectrum shown in FIG. 9.

In another embodiment, it is not uncommon for optical elements produced in a batch to have some variability within the batch, this may be compounded with ICE since the layer structure is generally arbitrary to any metric other than the spectroscopic data to which they were designed. An annealing process may be used to selectively shift the as fabricated spectrum of individual ICE from a batch to improve the yield of acceptable ICE in the batch. In one example, looking at the batch of second ICE described above, samples of the batch of the second ICE may be tested to determine the fabrication variability of the as-fabricated spectrum of each ICE at the standard temperature as compared to the designed red shifted spectrum. If the resulting spectra are sufficiently close, the same annealing process, described above, may be performed. However, if there is an unacceptable spread in the as-fabricated spectra at standard temperature, it may be possible to modify the annealing process to obtain an acceptable yield from the batch. For example, individual ICE from the batch may be annealed at different annealing temperatures, and/or for different times to obtain an acceptable spectrum. In one example, an ICE with an unacceptable spectrum may be annealed at stepwise increasing temperatures to iteratively shift the spectrum toward the desired target spectrum. FIG. 9 show an example of two ICE incorporating the same red shifted design discussed with respect to FIG. 5. The variation of the two as fabricated spectra, 502 and 902, shows a variation due to fabrication variability. Spectrum 502 corresponds to the as fabricated second ICE discussed above where the as fabricated spectrum matches the red shifted design spectrum, such that annealing for 12 hours at 300 C results in a near match to the target spectrum. Spectrum 902 corresponds to a second sample of the batch of second ICE where the as fabricated spectrum deviates from the desired designed spectrum 502. In this case, see FIG. 10, multiple annealing steps may be used to shift the as fabricated spectrum to spectrum 903 and again to spectrum 904. Each ICE, from the batch of second ICE, that deviate from the desired red shifted spectrum 502, may require different time and temperature annealing steps. A database of such conditions may be generated and a predictive correlation may be generated to correlate the annealing requirements for shifting different as fabricated spectrum to the target spectrum 301.

The invention claimed is:

1. A method for fabrication control of an integrated computational element comprising:
    fabricating a first integrated computational element to generate a target optical spectrum, the integrated computational element having a plurality of optical material layers wherein each layer has at least one material parameter of interest;
    measuring an as-fabricated optical spectrum of the first integrated computational element at a standard temperature; wherein the standard temperature is a testing temperature for the as-fabricated optical spectrum and wherein the testing temperature is a temperature within the anticipated operating temperature range for the first integrated computational element;
    annealing the first integrated computational element to a first predetermined annealing temperature for a first predetermined time;
    measuring the as-annealed optical spectrum of the first integrated computational element at the standard temperature;
    generating a transfer function relating a wavelength shift of the as-annealed optical transmission spectrum at the standard temperature compared to the as-fabricated optical transmission spectrum at the standard temperature; wherein the transfer function is a mathematical function illustrating the transformation or translation of the wavelength shift of the as-fabricated optical transmission spectrum to the as-annealed optical transmission spectrum;
    fabricating a second integrated computational element using the transfer function to modify at least one of the material parameters of interest of at least one of the plurality of optical material layers to shift a second as-annealed optical transmission spectrum of the second integrated computational element to match the target optical spectrum; and
    annealing the second integrated computational element to the first predetermined annealing temperature for the first predetermined time.

2. The method of claim 1 wherein the at least one material parameter of interest is selected from the group consisting of: a material thickness and an index of refraction.

3. The method of claim 1 wherein each of the plurality of material layers is made of an optical material chosen from the group consisting of: silicon, quartz, niobia, niobium, germanium, germania, $Al_2O_3$, $TiO_2$ and MgF.

4. The method of claim 1 wherein the target optical spectrum is related to a predetermined analyte.

5. The method of claim 1 wherein the transfer function comprises a wavelength shift related to a wavelength difference between at least one corresponding peak of the as-fabricated optical spectrum at the standard temperature of the first integrated computational element and the as-annealed optical spectrum at the standard temperature of the first integrated computational element.

6. The method of claim 1 wherein the plurality of optical material layers comprises alternating relatively high and low index of refraction optical materials.

7. The method of claim 1 wherein the second integrated computational element comprises a batch of second integrated computational elements and each element of the batch is annealed at the first predetermined annealing temperature for the first predetermined annealing time.

8. The method of claim 7 wherein the batch of second integrated computational optical elements comprises a plurality of batches of second integrated computational elements and each element of each batch is annealed at the first predetermined annealing temperature for the first predetermined annealing time.

9. A method for fabrication control of a batch of an integrated computational element comprising:
    fabricating a first integrated computational element to transmit a target optical spectrum, the integrated computational element having a plurality of optical material layers wherein each layer has at least one material parameter of interest;
    measuring an as-fabricated optical spectrum of the first integrated computational element at a standard temperature; wherein the standard temperature is a testing temperature for the as-fabricated optical spectrum and wherein the testing temperature is a temperature within the anticipated operating temperature range for the first integrated computational element;
    annealing the first integrated computational element to a first predetermined annealing temperature for a first predetermined time;
    measuring the as-annealed optical spectrum of the first integrated computational element at the standard temperature;
    generating a transfer function relating a wavelength shift of the as-annealed optical spectrum at the standard temperature compared to the as-fabricated optical spectrum at the standard temperature; wherein the transfer function is a mathematical function illustrating the transformation or translation of the wavelength shift of the as-fabricated optical transmission spectrum to the as-annealed optical transmission spectrum;

using the transfer function to modify at least one of the material parameters of interest of at least one of the plurality of optical material layers to shift an as-annealed optical spectrum of a second integrated computational element to match the target optical spectrum;

fabricating a batch of the second integrated computational elements and measuring the as-fabricated optical spectrum for each element of the batch at the standard temperature; and annealing each element of the batch of second integrated computational elements at an individual annealing temperature to shift the as-annealed optical spectrum of each second integrated computational element toward the target optical spectrum.

10. The method of claim 9 wherein the at least one material parameter of interest is selected from the group consisting of: a material thickness and an index of refraction.

11. The method of claim 9 wherein each of the plurality of material layers is made of an optical material chosen from the group consisting of: silicon, quartz, niobia, niobium, germanium, germania, $Al_2O_3$, $TiO_2$ and MgF.

12. The method of claim 9 wherein the target optical spectrum is related to a predetermined analyte.

13. The method of claim 9 wherein the transfer function comprises a wavelength shift related to a wavelength difference between at least one corresponding peak of the as-fabricated optical spectrum at the standard temperature of the first integrated computational element and the as-annealed optical spectrum at the standard temperature of the first integrated computational element.

* * * * *